US012131217B2

(12) United States Patent
Butterworth et al.

(10) Patent No.: US 12,131,217 B2
(45) Date of Patent: Oct. 29, 2024

(54) AUTOMATED SYSTEM FOR ACQUIRING IMAGES OF ONE OR MORE CAPILLARIES IN A CAPILLARY BED

(71) Applicant: Leuko Labs, Inc., Boston, MA (US)

(72) Inventors: Ian Butterworth, Somerville, MA (US); Carlos Castro-Gonzalez, Cambridge, MA (US); Aurelien Bourquard, Madrid (ES); Alvaro Sanchez Ferro, Madrid (ES); Ganimete Lamaj, Cambridge, MA (US); Nolan Bell, Somerville, MA (US); Ryan Benasutti, Milford, NH (US); Alberto Pablo-Trinidad, Madrid (ES)

(73) Assignee: LEUKO LABS, INC., Boston, MA (US)

( * ) Notice: Subject to any disclaimer, the term of this patent is extended or adjusted under 35 U.S.C. 154(b) by 0 days.

(21) Appl. No.: 17/878,128

(22) Filed: Aug. 1, 2022

(65) Prior Publication Data

US 2023/0032932 A1    Feb. 2, 2023

Related U.S. Application Data

(60) Provisional application No. 63/228,338, filed on Aug. 2, 2021.

(51) Int. Cl.
*G06K 7/10* (2006.01)
*G02B 19/00* (2006.01)

(52) U.S. Cl.
CPC ..... *G06K 7/10732* (2013.01); *G02B 19/0085* (2013.01)

(58) Field of Classification Search
CPC .......................... G06K 7/10732; G02B 19/085
USPC ......................................................... 235/454
See application file for complete search history.

(56) References Cited

U.S. PATENT DOCUMENTS

| 5,598,842 A * | 2/1997 | Ishihara ................. G01N 21/53 |
| | | 600/479 |
| 8,145,286 B2 | 3/2012 | Arai et al. |
| 11,244,452 B2 | 2/2022 | Castro-Gonzalez et al. |
| 2006/0161063 A1 | 7/2006 | Shau |

(Continued)

FOREIGN PATENT DOCUMENTS

WO    2021015843 A1    1/2021

OTHER PUBLICATIONS

Written Opinion of the International Searching Authority for International Application No. PCT/US2022/039000, dated Oct. 26, 2022, eight (8) pages.

*Primary Examiner* — Allyson N Trail
(74) *Attorney, Agent, or Firm* — Iandiorio Teska & Coleman, LLP

(57) ABSTRACT

An automated system for acquiring images of one or more capillaries in a capillary bed includes a platform for receiving a body portion of a subject, an imaging subsystem having a repositionable field of view and coupled to the platform to acquire images of at least a capillary bed of the body portion and a controller communicably coupled to the imaging subsystem to automatically reposition the field of view of the imaging subsystem to different areas of the capillary bed, and at each field of view within the capillary bed, activate the imaging subsystem to acquire images of one or more capillaries in the capillary bed.

37 Claims, 14 Drawing Sheets

(56) References Cited

U.S. PATENT DOCUMENTS

| | | | |
|---|---|---|---|
| 2016/0249812 A1* | 9/2016 | Wang | G01N 29/0681 |
| | | | 600/407 |
| 2019/0139221 A1* | 5/2019 | Castro-Gonzalez | ......... |
| | | | A61B 5/0261 |
| 2019/0247851 A1* | 8/2019 | Virey | B01L 3/502715 |
| 2021/0374963 A1* | 12/2021 | Gonzalez | G16H 50/20 |
| 2022/0061691 A1* | 3/2022 | Kawata | G01R 33/5608 |
| 2022/0406462 A1* | 12/2022 | Haase | G16H 20/60 |
| 2023/0032932 A1* | 2/2023 | Butterworth | G02B 19/0085 |
| 2023/0200693 A1* | 6/2023 | Cafferty | A61B 5/150946 |
| | | | 600/584 |
| 2023/0233156 A1* | 7/2023 | Mizuno | A61B 10/00 |
| | | | 600/479 |
| 2023/0264262 A1* | 8/2023 | Rusek | B22F 10/10 |

\* cited by examiner

AUTOMATED SYSTEM FOR ACQUIRING IMAGES OF ONE OR MORE CAPILLARIES IN A CAPILLARY BED

RELATED APPLICATIONS

This application claims benefit of and priority to U.S. Provisional Application Ser. No. 63/228,338 filed Aug. 2, 2021, under 35 U.S.C. §§ 119, 120, 363, 365, and 37 C.F.R. § 1.55 and § 1.78, which is incorporated herein by this reference.

GOVERNMENT RIGHTS

This invention was made with U.S. Government support under Grant No. R44CA228920 awarded by the National Cancer Institute SBIR Program and Grant No. U54HL143541 awarded by the National Institute of Health. The Government may have certain rights in the subject invention.

FIELD OF THE INVENTION

This invention relates to an automated system and method for acquiring images of one or more capillaries in a capillary bed.

BACKGROUND OF THE INVENTION

Conventional systems and methods for analyzing blood cell dynamics in non-invasive hematological measurements, e.g., as disclosed in U.S. Pat. No. 9,984,277 and U.S. Publication No. 2019/0139221, incorporated by reference herein, teach how to perform white blood cell measurements from non-invasive images of capillaries. However, the acquisition of images as disclosed in the '277 Patent and '221 Publication require manual operation of the imaging system by a skilled technician capable of determining the optimal location of capillaries to be imaged and to correct the focus, illumination, exposure time, operating rate, and the like, to produce images of sufficient quality to render a successful measurement of white blood cell count (WBC) and/or neutropenia and/or other blood parameters including red blood cells, hemoglobin, hematocrit, platelets, and the like.

In order to make such measurements available to unsupervised patients in a clinical setting or at home, the processes discussed above performed by the skilled technician needs to be automated. Thus, there is a need for an automated system and method to perform such measurements to determine WBC and/or neutropenia and/or other blood parameters without requiring intervention of a skilled technician.

SUMMARY OF THE INVENTION

In one aspect an automated system for acquiring images of one or more capillaries in a capillary bed is featured. The system includes a platform for receiving a body portion of a subject, an imaging subsystem having a repositionable field of view and coupled to the platform to acquire images of at least a capillary bed of the body portion, and a controller communicably coupled to the imaging subsystem to automatically reposition the field of view of the imaging subsystem to different areas of the capillary bed, and at each field of view within the capillary bed, activate the imaging subsystem to acquire images of one or more capillaries in the capillary bed.

In one embodiment, the controller may be configured to process the images of each said area and assign a location and confidence of one or more high-quality capillaries in each said area. The information from each field of view may be stitched together by the controller to produce a distribution of capillary locations, capillary sizes, and confidence levels of capillary existence across a super field of view. The controller may be configured to process said distribution of capillary locations and confidence levels and determine a location and/or size of an optimal field of view for recording a set of images or videos of high-quality capillaries. The images may be stitched together by the controller across a super field of view to produce a single image and the controller may detect the capillary locations, sizes and confidence levels in that single image. The body portion of the subject may include one of: a finger, a toe, a tongue, a lip, a gum, or an earlobe of the subject. The body portion may include the nailfold of the finger or the toe. The location of the super field of view capillary distribution plot may be acquired from a middle bottom location of the nailfold. The controller may be configured to automatically calibrate the imaging subsystem by setting the imaging subsystem to a predetermined start location. The controller may be configured to automatically adjust the exposure time of the imaging subsystem. The controller may be configured to automatically adjust the gain of the imaging subsystem. The controller may be configured to automatically adjust the focus of the imaging subsystem. The controller may be configured to automatically ensure the imaging subsystem is operating at a desired rate. The controller may be configured to automatically ensure illumination of at least capillary bed is within a predetermined illumination range. The controller may be configured to automatically ensure the exposure time is within a predetermined exposure time range. The controller may be configured to automatically ensure the imaging system gain is within a predetermined range. The controller may be configured to automatically ensure the focusing is within a predetermined focusing range. The controller may be configured to control one or more light sources of the imaging system to emit light at one or more selected wavelengths or wavelength ranges. The controller may be configured to select one or more wavelengths or wavelength ranges based on image quality. The controller may activate or not activate the imaging system based on the quality of the images of the capillary bed. The controller may activate the imaging system to acquire the images including one or more capillaries in the capillary bed for a period of time based on the number of optical adsorption gaps (OAGs) detected in one or more capillaries. The controller communicably coupled to the imaging subsystem may be configured to detect finger movement in the platform by the imaging subsystem.

In another aspect a method for acquiring images of one or more capillaries in a capillary bed is featured. The method includes receiving a body portion of a human subject, acquiring images of at least a capillary bed of the body portion with a repositionable field of view, automatically repositioning the field of view to different areas of the capillary bed, and at each field of view within the capillary bed, acquiring images of one or more capillaries in the capillary bed.

In one embodiment, the method may include processing the images of each said area and assigning a location and confidence level of one or more high-quality capillaries in each said area. The information from each field of view may be stitched together to produce a distribution of capillary locations, capillary sizes, and confidence levels of capillary existence across a super field of view. The method may include processing said distribution of capillary locations and confidence levels and determining a location and/or size of an optimum field of view for recording a set of images of high-quality capillaries. The images may be stitched together by the controller across a super field of view to produce a single image and detecting capillary locations, sizes, and confidence levels in that single image. The super field of view capillary distribution plot may be acquired from a middle bottom location of a nailfold. The method may include automatically calibrating the imaging to a predetermined start location. The method may include automatically adjusting the exposure time. The method may include automatically adjusting the imaging system gain. The method may include automatically adjusting the focus. The method may include automatically ensuring the imaging is at a desired rate. The method may include automatically ensuring the illumination of at least the capillary bed is within a predetermined illumination range. The method may include automatically ensuring the exposure time is within a predetermined exposure time range. The method may include automatically ensuring the imaging system gain is within a predetermined range. The method may include automatically ensuring focusing is within a predetermined focusing range then automatically emitting light at one or more selected wavelengths or wavelength ranges. The method may include selecting the one or more wavelengths or wavelength ranges may be based on image quality. The method may include activating or not activating the imaging based on the quality of images in the capillary bed. The method may include acquiring the images of one or more capillaries in the capillary bed for a period of time may be based on the number of optical absorption gaps detected in the one or more capillaries. The method may include detecting movement of a finger during the imaging.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
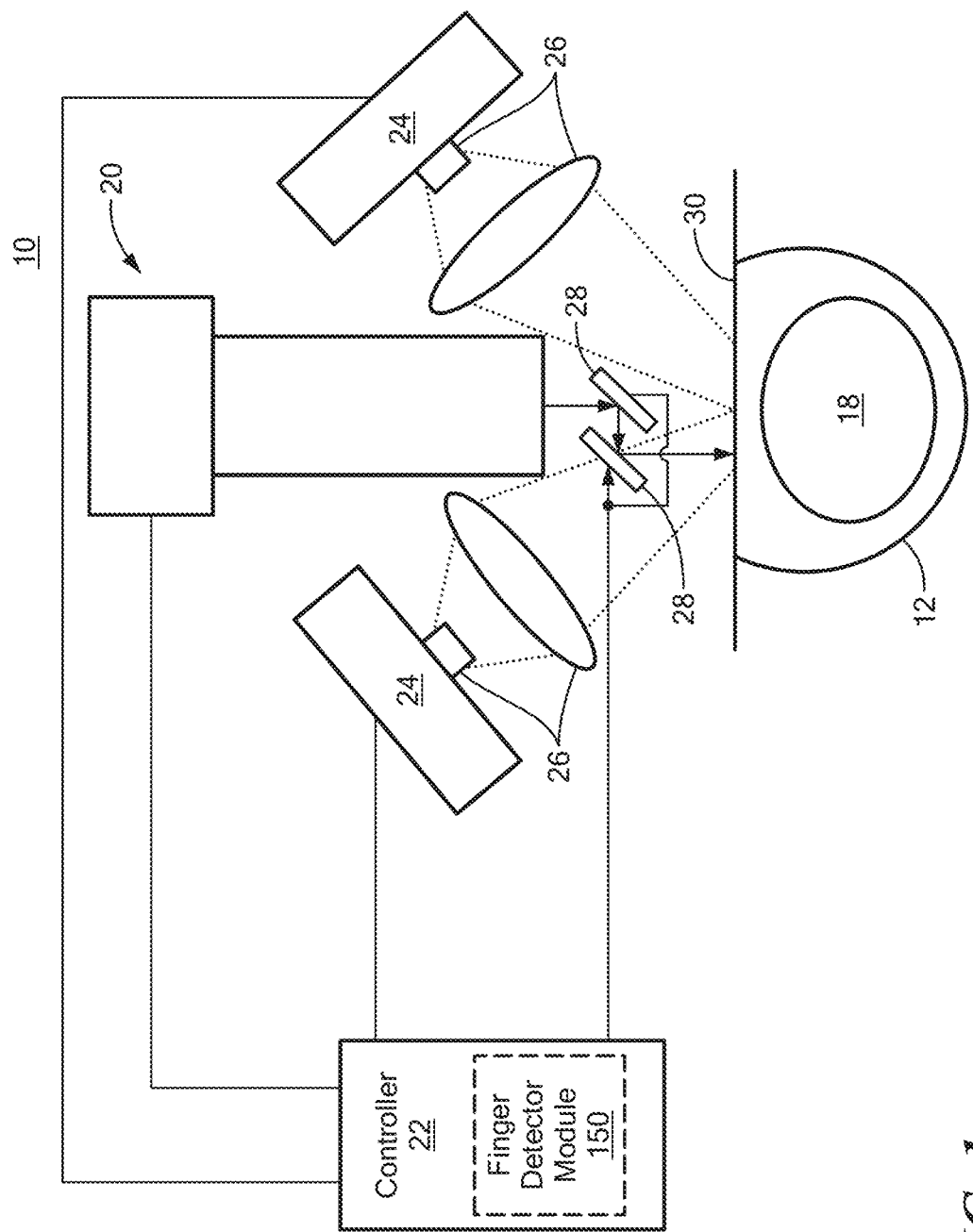
FIG. 1 is a schematic block diagram showing the primary components of one example of the automated system for acquiring images of one or more capillaries in a capillary bed.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2A:
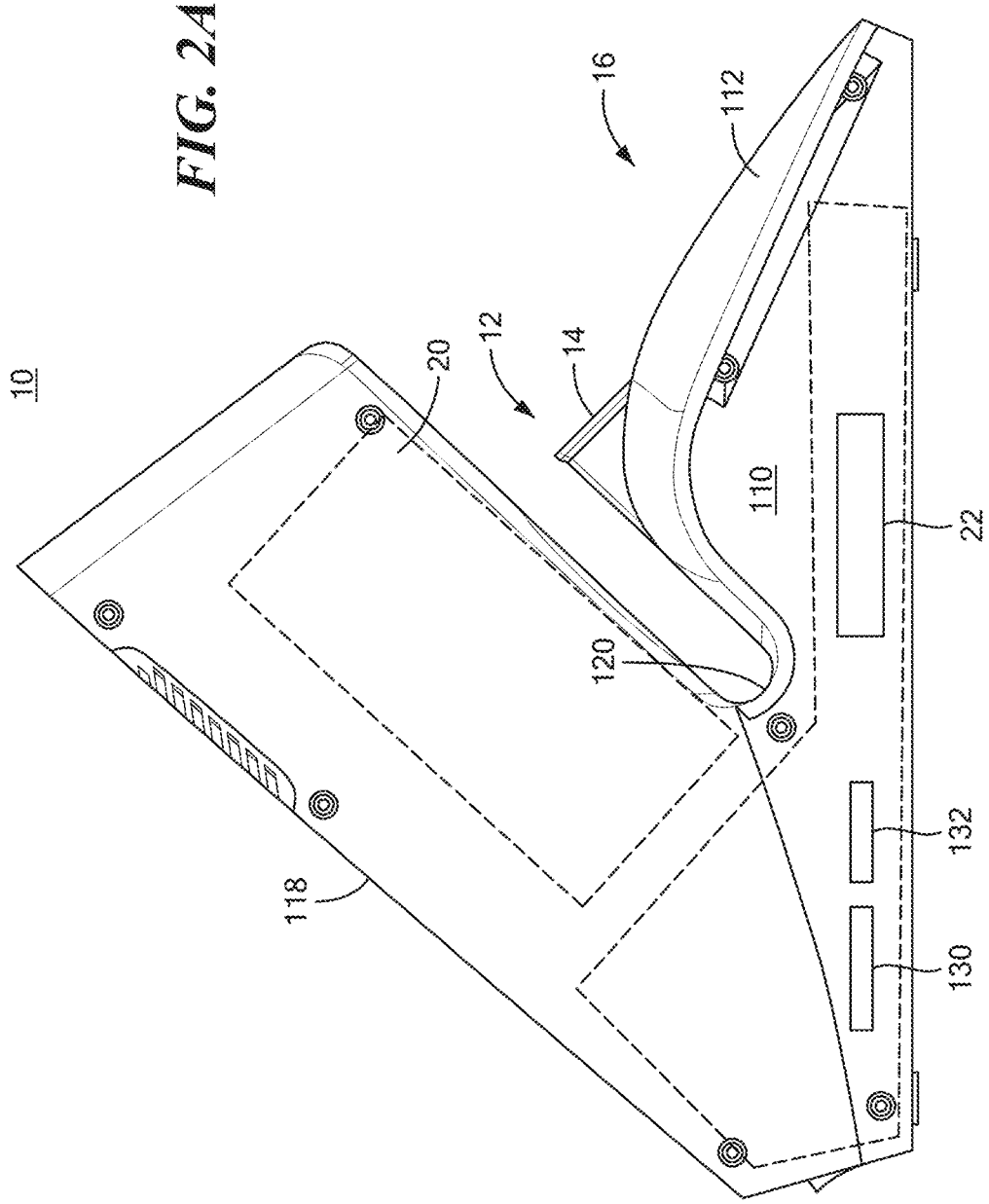
FIGS. 2A and 2B are schematic views showing in further detail the primary components of the system shown in FIG. 1.

There is shown in FIG. 1, one example of automated system 10 for acquiring images of one or more capillaries in a capillary bed. System 10 includes platform 12 for receiving a body portion of a subject. In one example, platform 12 may be a finger well, e.g., finger well 14, FIGS. 2A and 2B, disclosed in this example in ergonomic hand-holder 16 (discussed in further detail below). The body portion of the subject may include a finger, a toe, a tongue, a lip, a gum, or an earlobe of a human subject. FIG. 1 shows an example of a top view of finger 18 inserted into platform 12. FIG. 3 shows an example of finger 18 with capillary bed 36 to be automatically imaged by system 10.

Figure 2B:
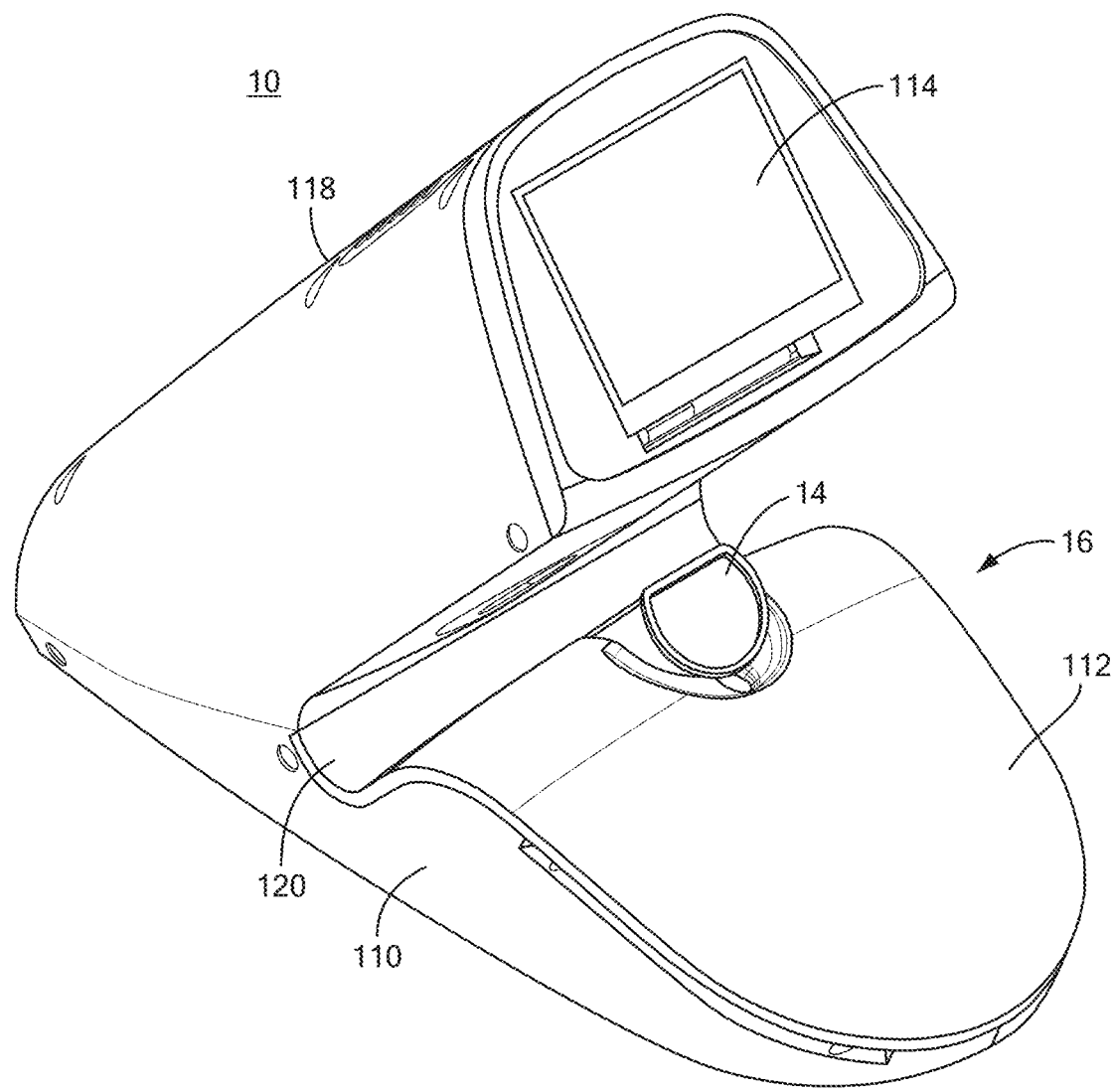
Figure 3:
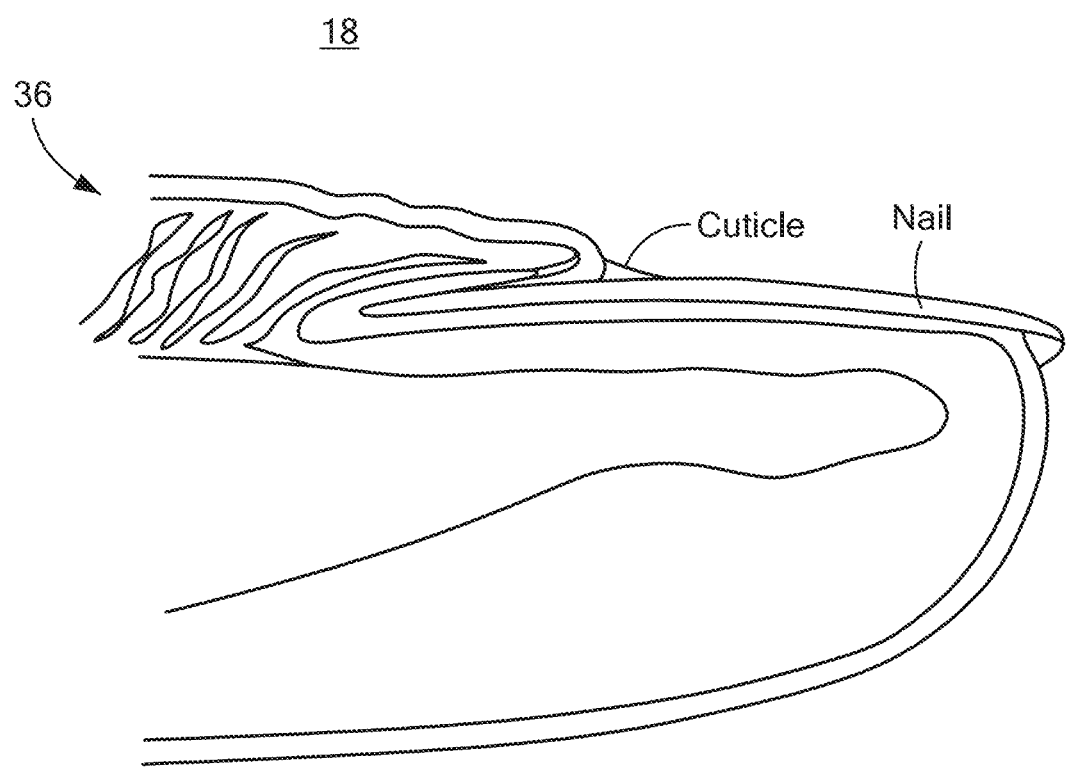
FIG. 3 shows an example of a capillary bed in a finger.

System 10, FIGS. 1-2B, also includes imaging subsystem 20 having a repositionable field of view (FOV) with an adjustable focus coupled to platform 12 and controller 22 as shown. Imaging subsystem 20 acquires images of at least a capillary bed of the body portion. Imaging subsystem 20 preferably includes one or more light emitting devices 24, e.g., light emitting diodes (LEDs) or similar type light emitting device, one or more focusing lenses 26, one or more scanning mirrors 28, and optical window 30 as shown.

Figure 4:
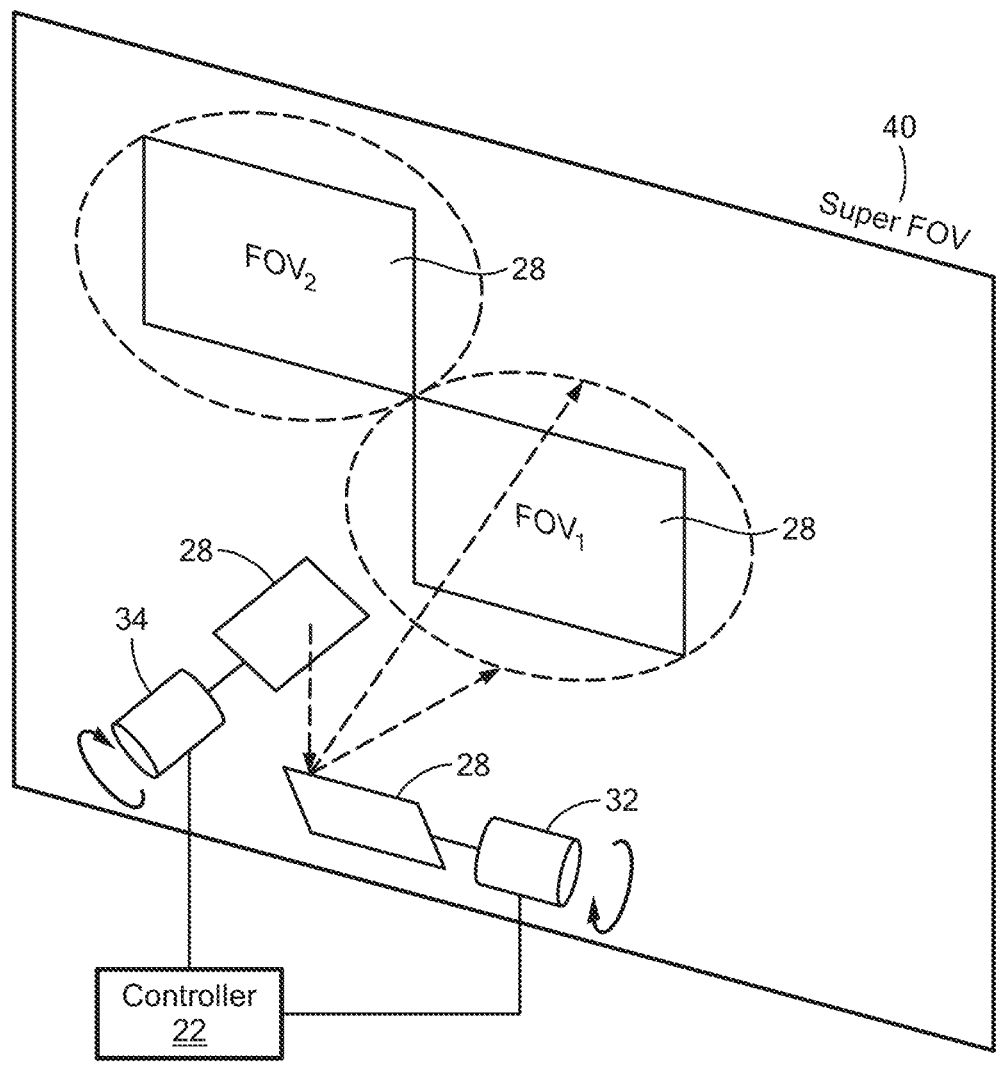
FIG. 4 shows one example of the controller shown in one or more of FIGS. 1-2B coupled to an x-axis motor and a y-axis motor coupled to scanning mirrors.
Figure 5:
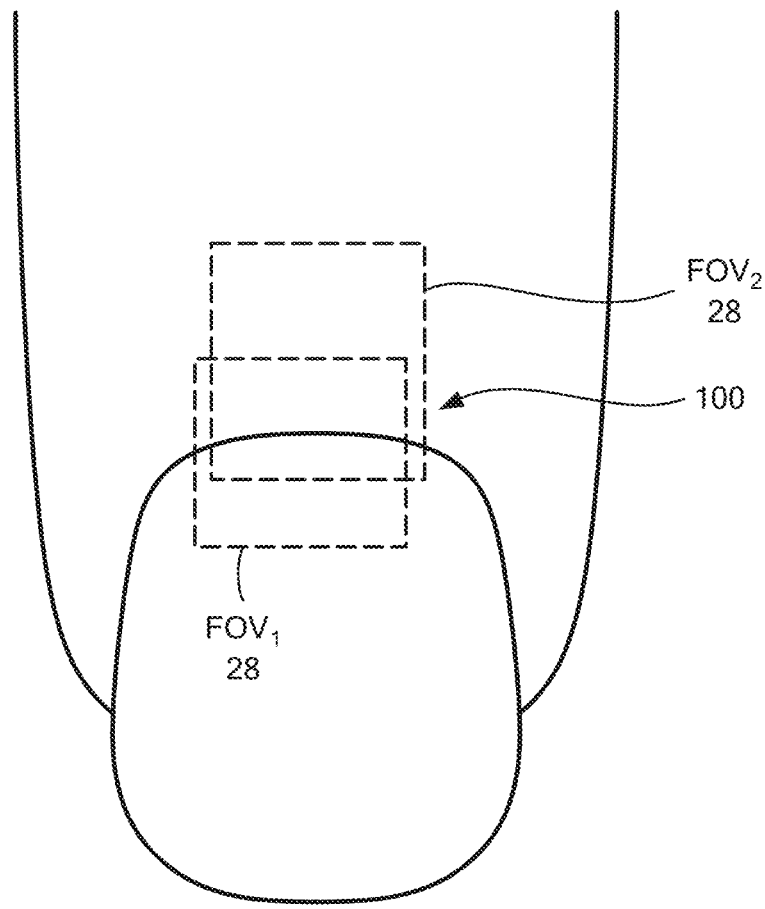
FIG. 5 shows an example of a repositionable field of view (FOV) repositioned to different areas of a capillary bed.

System 10 also includes controller 22, communicably coupled to imaging subsystem 20, one or more focusing lenses 26, and one or more scanning mirrors 28. Controller 22 automatically repositions the FOV of imaging subsystem 20 to different areas of the capillary bed. FIG. 4 shows one example of controller 22 coupled to X-axis motor 32 and Y-access motor 34 each preferably coupled to a scanning mirror 28 as shown. In this example, controller 22 automatically repositions repositionable FOV 28 to different areas or positions of a capillary bed, e.g., as shown by $FOV_1$ and $FOV_2$. FIG. 5 shows an example of repositionable FOV 28 repositioned to different areas of capillary bed 36, FIG. 3 of finger 18, e.g., $FOV_1$-28 and $FOV_2$-28. At each repositionable FOV 28 within capillary bed 18, controller 22, FIGS. 1 and 2A, activates imaging subsystem 20 to acquire images of one or more capillaries in capillary bed 36. In this example, repositionable FOV 28 is preferably repositioned by controller 22 to different areas of capillary bed 36, FIG. 3, of finger 18. In other examples, repositionable FOV 28 may be repositioned by controller 22 to different areas of capillary bed of a toe, a tongue, a lip, a gum, or an earlobe of a human subject.

Controller 22 may be a processor, one or more processors, an application-specific integrated circuit (ASIC), firmware, hardware, and/or software (including firmware, resident software, micro-code, and the like) or a combination of both hardware and software. Controller 22 preferably includes one or more programs stored in a memory which are configured to be executed by the one or more processors. Computer program code for the programs for carrying out the instructions or operation of controller 22 may be written in any combination of one or more programming languages, including but not limited to an object-oriented programming language, e.g., C++, Smalltalk, Java, and the like, or conventional procedural programming languages, such as the "C" programming language, Assembly language or similar programming languages.

Preferably, controller 22, FIGS. 1, 2A and 4, processes the images in each area of the capillary bed and assigns a location and confidence level to indicate the presence of one or more high-quality capillaries in each area. As disclosed herein, one or more high-quality capillaries preferably meets the requirements of one or more desired features, e.g., a high-quality capillary contains one or more optical absorption gaps (OAGs), are substantially parallel to the imaging plane, have a similar width to a white blood cell, have a sufficient length to allow for the passage of OAGs, have a high-quality contrast, are in focus, are well illuminated, and blood flow is preferably not restricted. Thus, high-quality capillaries are defined herein are preferably amiable for analysis to produce an accurate blood measurement including a white blood cell count, and/or neutropenia classification, and/or the subtype of any white blood cells and/or other blood parameters.

In one design, information from each FOV discussed above is preferably stitched together by controller 22 to produce a distribution of capillary locations, capillary sizes, and confidence levels of capillary existence across a super FOV. As defined herein, a super FOV is a geometric area across which the imaging FOV is repositioned.

Figure 6:
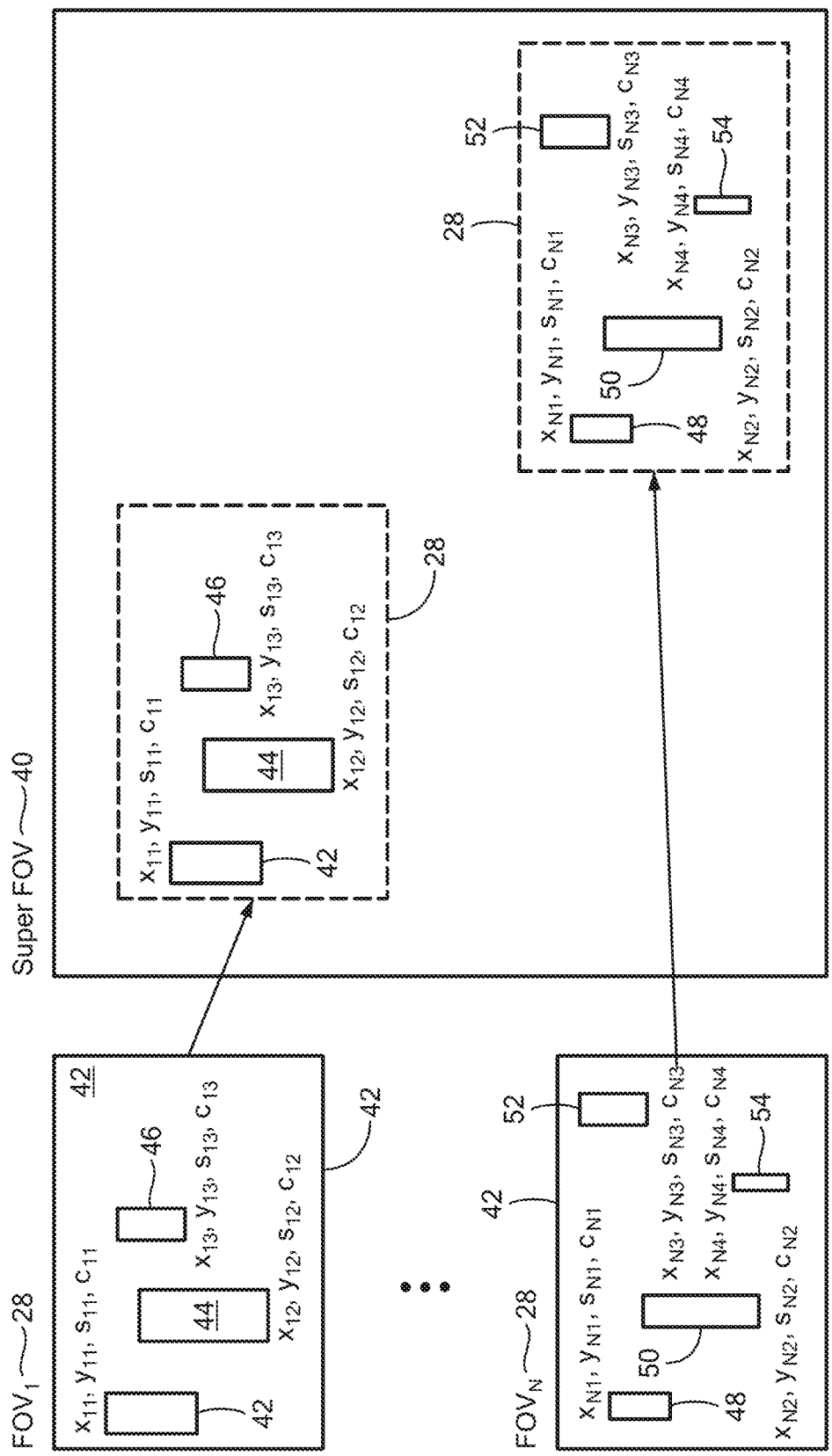
FIG. 6 shows an example of information from two FOVs stitched together by controller produce a distribution of capillary locations, capillary sizes, and confidence levels of capillary existence across a super FOV.

FIG. 6 show an example of $FOV_1$-28 to $FOV_N$-28 where information from each $FOV_1$-28 and $FOV_N$-28 is stitched together by controller 22 to produce a distribution of capillary locations, capillary sizes, and confidence levels of capillary existence across super FOV-40. In this example, the distribution of capillary locations, capillary sizes, and confidence levels of capillary existence for $FOV_1$-28 is shown in bounding boxes 42, 44, and 46, where x indicates the X-coordinate, y indicates the Y-coordinate, S indicates the capillary size (width and height), and C indicates the confidence level of the existence of a high-quality capillary. Similarly, for $FOV_N$-28, the distribution of capillary locations, capillary sizes, and confidence levels of capillary existence for $FOV_N$-28 is shown in bounding boxes 48, 50, 52, and 54, where x indicates the X-coordinate, y indicates the Y-coordinate, S indicates the capillary size (width and height), and C indicates the confidence level of the existence of a high-quality capillary.

As shown in example in FIGS. 4 and 6, the information from $FOV_1$-28 and $FOV_N$-28 is preferably stitched together by controller 22 to produce a distribution of capillary locations, capillary sizes, and confidence levels of capillary existence across super FOV 40.

Figure 7:
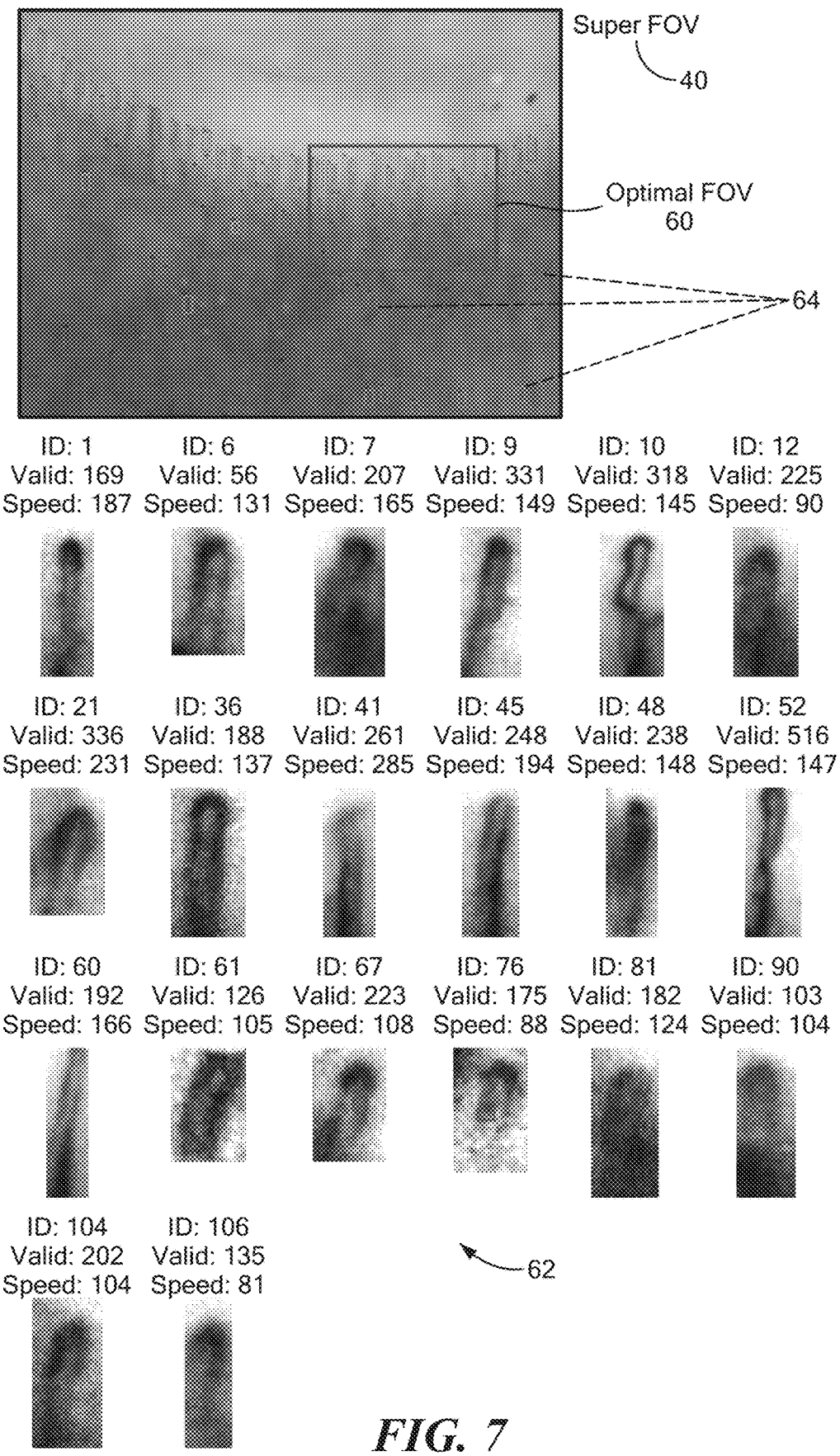
FIG. 7 shows an example of a super FOV, an optimal FOV, distributions of capillary location sizes and confidence levels, and capillaries within the optimal FOV to be analyzed.

Controller 22, FIGS. 1, 2A and 4, preferably processes the distribution of capillary locations, sizes, and confidence levels discussed above and determines a location and/or size of an optimal field of view for recording a set of images or videos of high-quality capillaries. FIG. 7 shows an example of super FOV 40 discussed above with reference to FIGS. 4 and 6 and examples of optimal field of view 60 for recording a set of images or videos of high-quality capillaries 62 to be analyzed to determine WBC count and/or neutropenia and/or white blood cell type and/or other blood parameters. The distribution of capillary locations, capillary sizes, and confidence levels of capillary existence across super FOV 40 in the bounding boxes discussed above with reference to FIG. 6 are also indicated generally at 64, FIG. 7.

In one example, optimal FOV 60, FIG. 7, for recording a set of images or videos of high-quality capillaries 62 may be determined by calculating the x-y coordinates of optimal FOV 60 and the width and height of optimal FOV 60 (x_opt, y_opt, w_opt, h_opt). To determine x_opt and y_opt, x_target and y_target are determined, where x_target is the weighted mean of x coordinates of detected capillaries weighted by their confidence levels and y_target is the weighted 95% percentile of the y coordinates of detected capillaries, where the weights are the confidences of each corresponding capillary. Then, x_opt equals x_target and y_opt equals y_target+0.25*h_FOV. In this example, w_opt equals w_FOV and h_opt equals h_fov, where w_FOV and h_FOV and the width and height of the fixed field of view of the imaging system.

In one design, images may be stitched together by controller 22, FIGS. 1, 2A and 4, across a super FOV to produce a single image and controller 22 preferably detects the capillary locations, sizes, and confidence levels in the single image.

Figure 8:
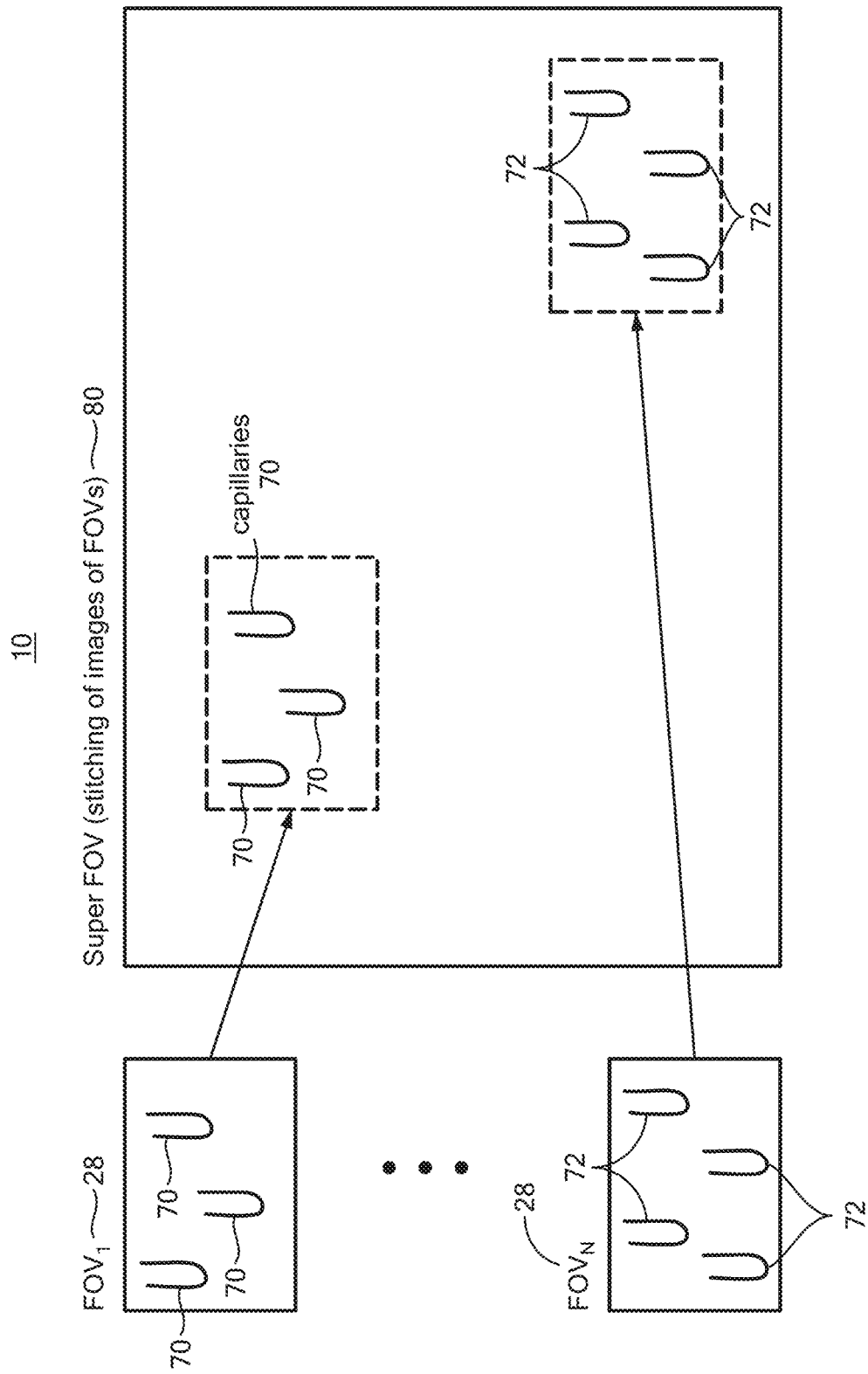
FIG. 8 shows am example of capillaries in multiple FOVs stitched together by the controller across a super FOV.

FIG. 8 shows one example of a depiction of images of one or more capillaries 70 for $FOV_1$-28 and a depiction of images of one or more capillaries 72 for $FOV_N$-28 which are stitched together by controller 22 across super FOV-80 as shown. Controller 22 preferably detects capillary locations, sizes, and confidence levels in the single image. The optimal FOV is determined as discussed above with reference to one or more FIGS. 1-7.

Figure 9:
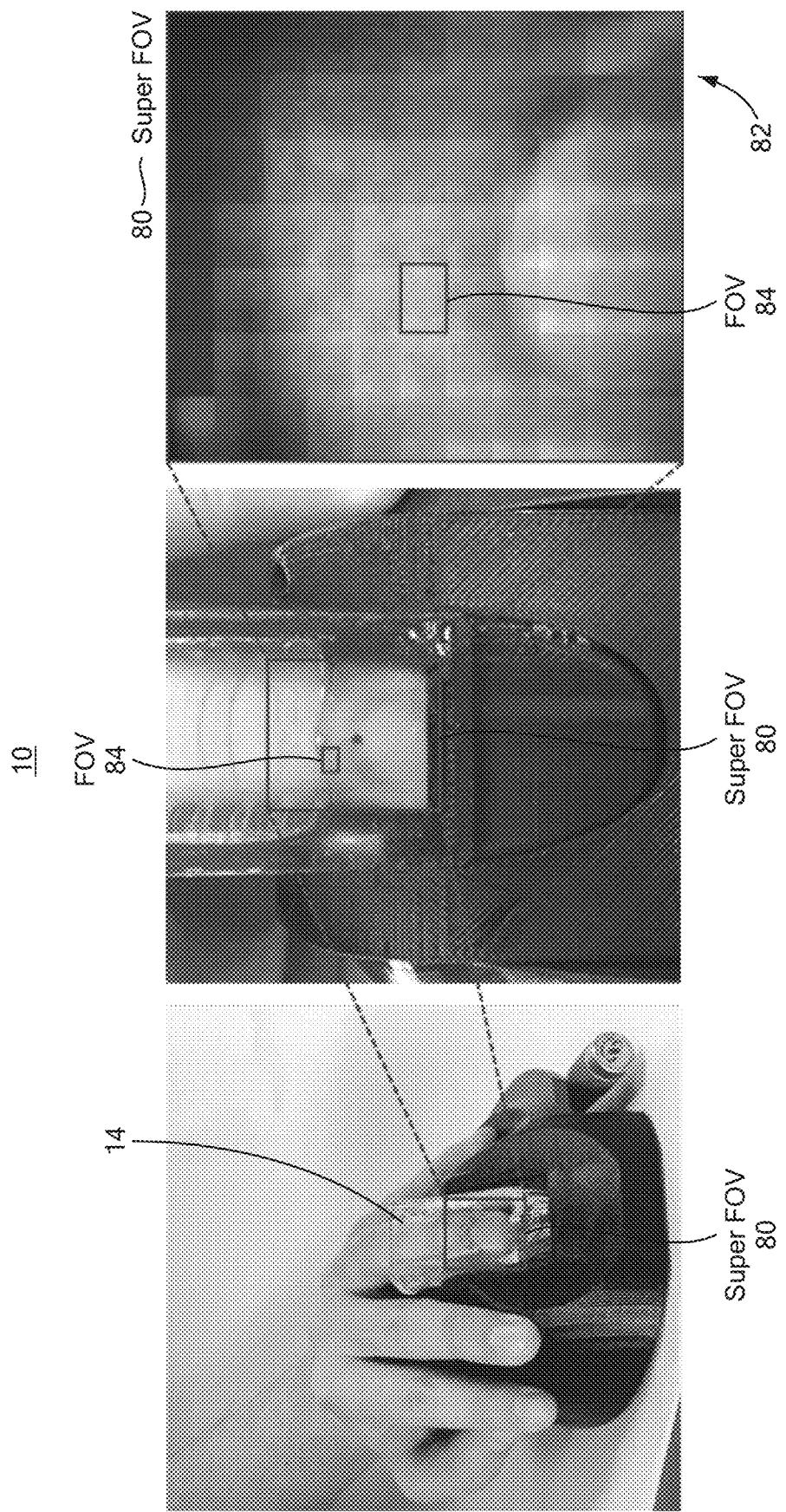
FIG. 9 shows an example of a prototype of the system shown in one or more of FIGS. 1-8 with a finger placed in a finger well and images stitched together by the controller across a super FOV to produce a single image to detect the capillary locations, sizes and confidence levels in a single image.

FIG. 9 shows an example of a prototype of system 10 where a user has placed a finger in finger well 14 of platform 12 and images are stitched together by controller 22, FIGS. 1, 2A and 4, across a super FOV 80 to produce a single image 82 where controller 22 preferably detects the capillary locations, sizes, and confidence levels in the single image. An example of the optimal FOV is indicated at 84.

In one example, the super FOV of the capillary distribution plot discussed above with reference to one or more of FIGS. 1-9 may be acquired from the middle location of the nailfold, e.g., indicated generally at 100, FIG. 5.

FIGS. 2A and 2B show examples of a prototype of system 10 configured as ergonomic hand-holder 16. System 10 preferably includes base section 110 including convex hand support 112 with centrally located downwardly oriented removable finger well or tube 14 for receiving a finger of a human subject as shown or other body portion of the subject including one of: a finger, a toe, a tongue, a lip, a gum, or an earlobe of the subject. System 10 also preferably includes angled section 118 extending upwardly over disposable finger well or tube insert 14 terminating in display screen 114, FIG. 2B. Angled section 118 also preferably includes imaging subsystem 20, shown in on or more of FIGS. 1-2B. In this example, base section 110, also preferably includes controller 22, power board 130, FIG. 2B and input/output board 132.

In one example, convex hand support 112 slopes upward from base section 110 and extends downwardly to intersection 120 between base section 110 and angled section 118. In one example, the intersection is radiused as shown. In one example, convex hand support 112 may include replaceable pads to accommodate various hand sizes. Additional details of finger well 14 shown in at least FIGS. 2A and 2B are disclosed in U.S. Pat. No. 11,160,492, by one of the inventors hereof, incorporated by reference herein.

Imaging subsystem 20 preferably acquires and processes images and/or videos of one or more high quality capillaries of a capillary bed of a finger in removal finger well or tube insert 14 to determine a blood measurement including a white blood cell (WBC) count and/or neutropenia classification and/or WBC type and/or other blood parameters.

Figure 10:
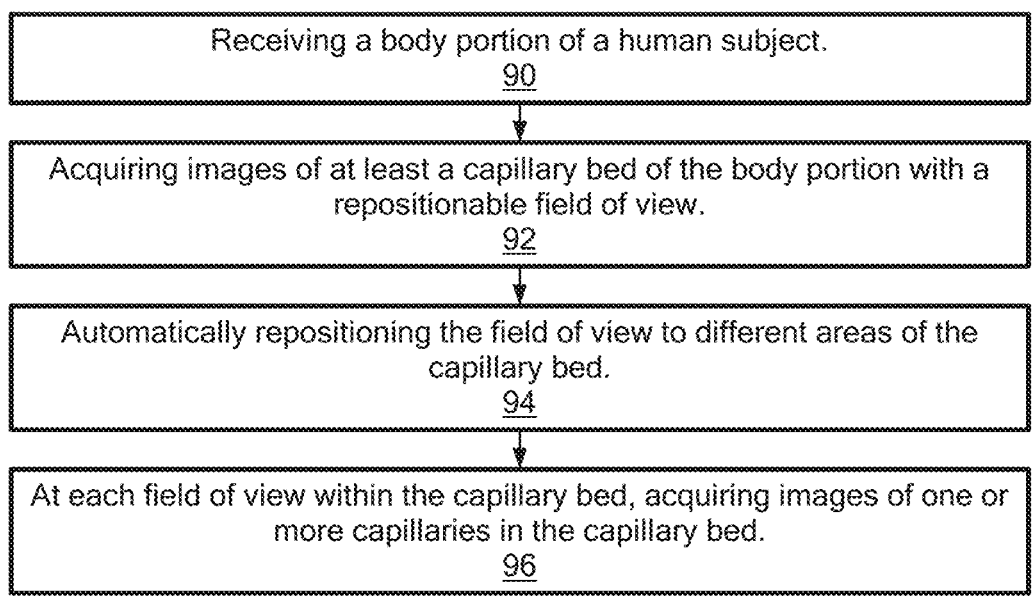
FIG. 10 is a flow chart showing one example of the method for acquiring images of one or more capillaries in a capillary bed.

One example of the method for acquiring images of one or more capillaries in a capillary bed includes receiving a body portion of a human subject, step 90, FIG. 10. The method also includes acquiring images of at least a capillary bed of the body portion with a repositionable field of view FOV, step 92. The method also includes automatically repositioning the FOV to different areas of the capillary bed, step 94. The method also includes at each FOV within the capillary bed, acquiring images of one or more capillaries in the capillary bed.

In one design, controller 22, FIGS. 1, 2A and 4, preferably automatically calibrates imaging subsystem 20 by setting imaging subsystem 20 to a predetermined start location. Controller 22 may also automatically adjust the exposure time of the imaging subsystem 20, may automatically adjust the focus of the imaging subsystem 20, and/or may ensure imaging subsystem 20 is operating at a desired rate, e.g., frames per second. Controller 22 may also automatically ensure the illumination of the one or more capillary bed is within a predetermined illumination range, automatically ensure the exposure time is within a predetermined exposure time, and/or automatically ensure the focusing is within a predetermined focusing range. Controller 22 also preferably controls the one or more light sources 24, FIG. 1, of imaging subsystem 20 to emit light at one or more selected wavelengths or wavelength ranges. Preferably, controller 22 selects one or more wavelengths or wavelength ranges based on image quality.

System 10 and the method thereof discussed above with reference to one or more of FIGS. 1-10 preferably includes software or computer code that provides for wavelength selection to select the optimal wavelength for imaging quality preferably on a per-measurement basis. Wavelength selection is preferably determined during the setup phase before each measurement. Wavelength selection preferably determines the optimal wavelength by evaluating an imaging quality metric using each available wavelength. The wavelength with the greater metric value is then selected.

Wavelength selection preferably maximizes acquisition success over a wide range of skin characteristics, including, inter alia, pigmentation levels across the Fitzpatrick skin phototype scale, and local pigmentations such as freckles. Without an automatic wavelength selection procedure by system 10, wavelength selection would need to be performed manually by a trained technician. Minimizing cost and maximizing ease of use of system 10 for both the patient and the care team are important objectives.

Figure 11:
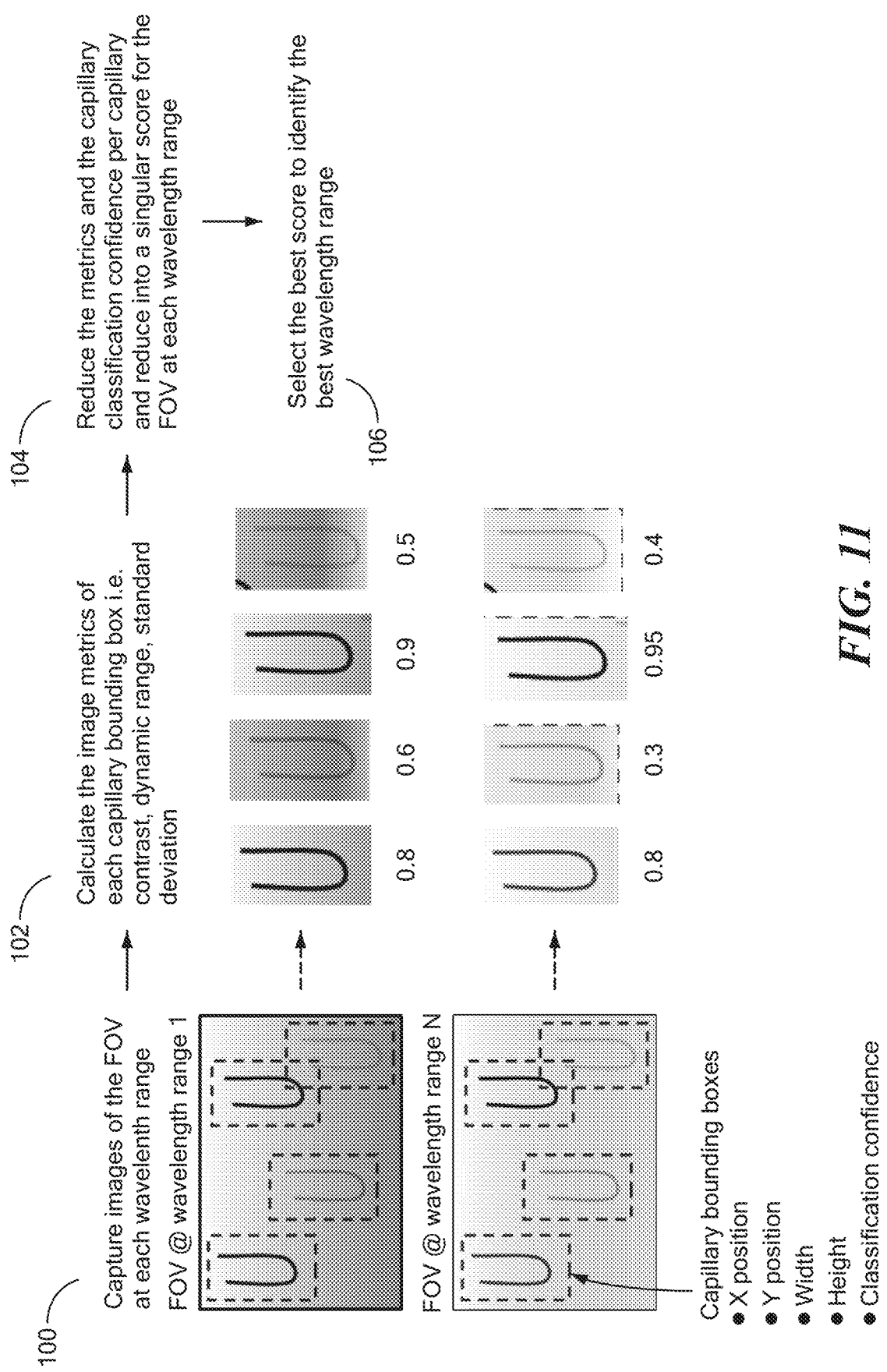
FIG. 11 is a schematic block diagram showing one example an automated wavelength selection for the system and method shown in one or more of FIGS. 1-10.

In one example, controller 22 is preferably configured to automatically selects the appropriate wavelength. Such an automated procedure additionally ensures that the correct methodology is preferably followed. In one example, the wavelength selection performed by controller 22 preferably includes running a setup procedure using illumination with spectral content in the approximate range, e.g., about 540-580 nm illumination (wavelength range 1). At the final target FOV and after auto-exposure and auto-gain have settled, one frame is captured using wavelength range 1, step 100, FIG. 11. Illumination is preferably switched to in the approximate range, e.g., about 405-430 nm illumination (wavelength range 2). After auto-exposure and auto-gain have settled, one frame is captured using wavelength range 2. In each frame, capillaries are detected using an object detection routine to identify capillaries, create bounding boxes around the capillaries, and attribute a capillary confidence value, step 102. Capillaries above a given classification confidence threshold are then evaluated for imaging contrast by running a contrast algorithm on the image regions identified by the capillary bounding boxes. A single metric for each capillary is made by taking the product of the capillary confidence and the capillary contrast. A single score for each wavelength's FOV is preferably then taken by taking the sum of the capillary scores, step 104. The range that has the highest metric value is identified, and switched to the associated illumination regime, step 106. After auto-exposure and auto-gain have settled, finish the setup procedure. See FIG. 11.

Controller 22 may activate or not activate imaging subsystem 20 based on the quality of images in the capillary bed. Controller 22 may activate imaging subsystem 20 to acquire images of one or more capillaries in the capillary bed for a period of time based on the number of OAGs detected in the one or more capillaries.

Users of system 10 need to keep their finger still in finger well 14, FIGS. 2A-2B, while a measurement is taken. Some users may experience difficulty following this instruction and may either remove their finger prematurely or move their finger in finger well 14 during the measurement. If the finger movement is excessive, the analysis performed by system 10 may be suboptimal so it is recommended that the user repeat the measurement without any movement.

To address this problem, controller 22 communicably coupled to imaging system 20 preferably detects movement of a finger within finger well 14 using imaging subsystem 20. Controller 22 preferably includes software or computer code configured as finger movement detector module 150, FIG. 1, capable of detecting problematic finger movement. Finger movement detection is preferably used at the end of every measurement to determine if the pre measurement needs to be repeated due to excessive finger movement. Finger movement detector module 150 preferably operates by assessing the movement between pairs of video frames from the measurement. An error is raised if the measured movement exceeds the allowable threshold.

Figure 12:
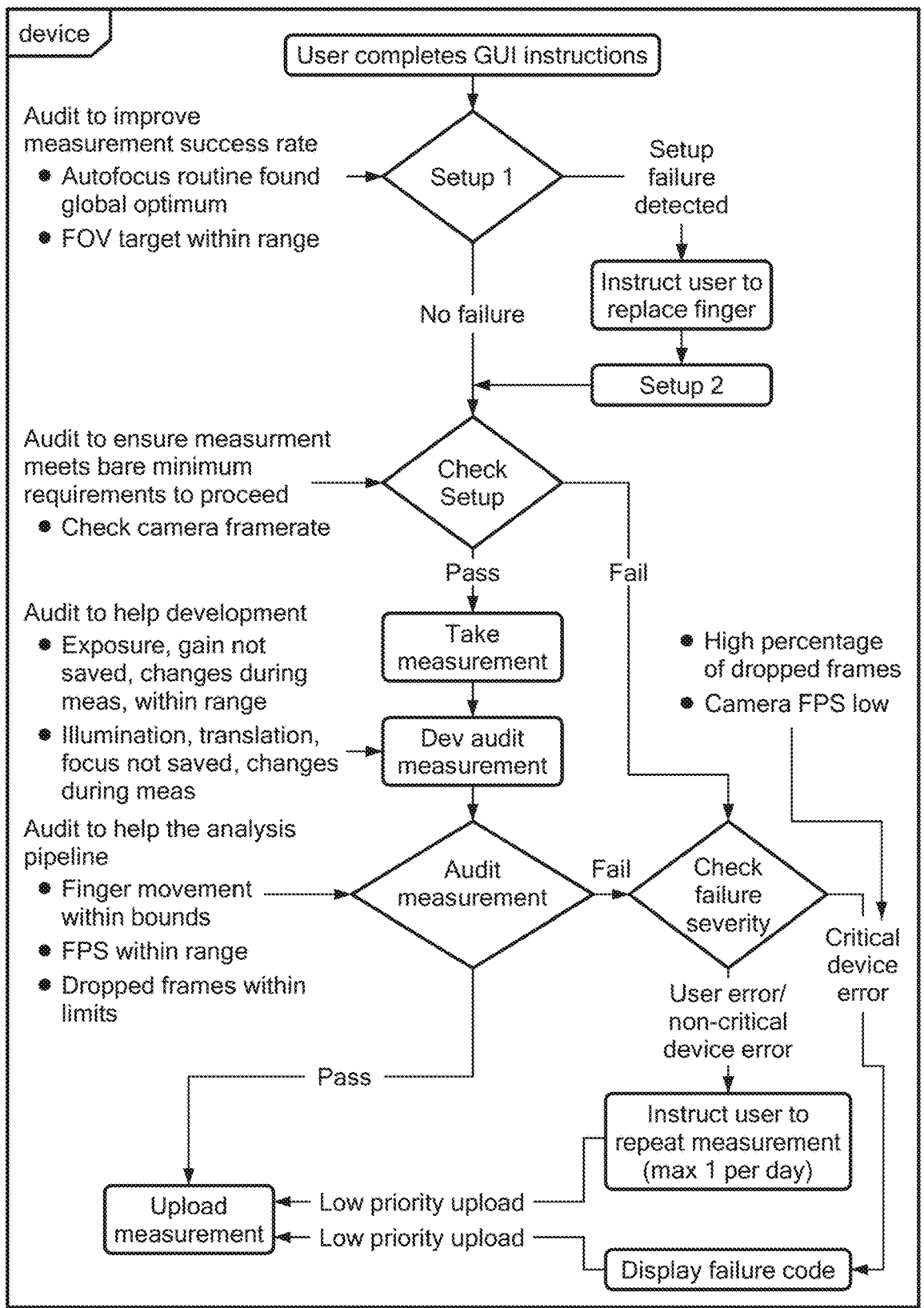
FIG. 12 is a flow chart showing one example of finger movement detection for the system and method shown in one or more of FIGS. 1-11.
Figure 12:
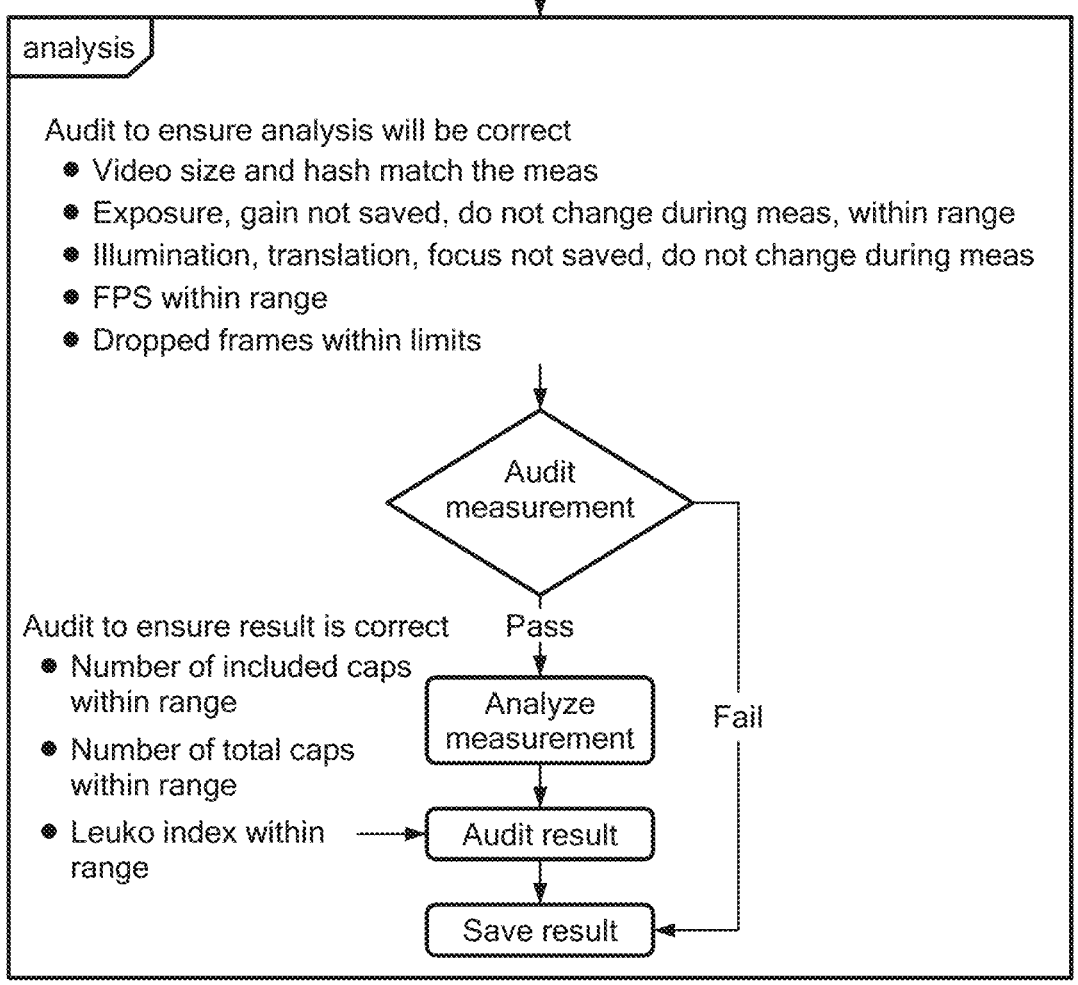

One example finger movement detector module 150 includes the steps of: 1) estimating high-frequency movement between all contiguous video frames in the measurement video, 2) estimating low-frequency movement between video frames spaced one second apart in the measurement video, 3) raising an error if any movement estimates exceed a threshold, and 4) estimating movement using Robinson's motion estimation algorithm. See e.g., Robinson, D., Milanfar, P., *Fast Local and Global Projection-Based Methods for Affine Motion Estimation*, Journal of Mathematical Imaging and Vision 18, 35-54 (2003), https://doi.org/10.1023/A:1021841127282, incorporated by reference herein. See FIG. 12.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. An automated system for acquiring images of one or more capillaries in a capillary bed, the system comprising:
    a platform for receiving a body portion of a subject;
    an imaging subsystem having a repositionable field of view and coupled to the platform to acquire images of at least a capillary bed of the body portion; and
    a controller communicably coupled to the imaging subsystem to:
        automatically reposition the field of view of the imaging subsystem to different areas of the capillary bed,
        at each field of view within the capillary bed, activate the imaging subsystem to acquire images of one or more capillaries in the capillary bed;
        process the images of each said area and assign a location and confidence of one or more high-quality capillaries in each said area; and
        wherein information from each field of view is stitched together by the controller to produce a distribution of capillary locations, capillary sizes, and confidence levels of capillary existence across a super field of view.

2. The system of claim 1 in which the controller is configured to process said distribution of capillary locations and confidence levels and determine a location and/or size of an optimal field of view for recording a set of images or videos of high-quality capillaries.

3. The system of claim 2 in which the location of the super field of view capillary distribution plot is acquired from a middle bottom location of the nailfold.

4. The system of claim 1 in which the images are stitched together by the controller across a super field of view to produce a single image and the controller detects the capillary locations, sizes and confidence levels in that single image.

5. The system of claim 1 in which the body portion of the subject includes one of: a finger, a toe, a tongue, a lip, a gum, or an earlobe of the subject.

6. The system of claim 5 in which the body portion includes the nailfold of the finger or the toe.

7. The system of claim 1 in which the controller is configured to automatically calibrate the imaging subsystem by setting the imaging subsystem to a predetermined start location.

8. The system of claim 1 in which the controller is configured to automatically adjust the exposure time of the imaging subsystem.

9. The system of claim 8 in controller is configured to automatically ensure the exposure time is within a predetermined exposure time range.

10. The system of claim 8 in controller is configured to automatically ensure the imaging system gain is within a predetermined range.

11. The system of claim 1 in which the controller is configured to automatically adjust a gain of the imaging subsystem.

12. The system of claim 1 in which the controller is configured to automatically adjust the focus of the imaging subsystem.

13. The system of claim 12 in controller is configured to automatically ensure the focusing is within a predetermined focusing range.

14. The system of claim 1 in which the controller is configured to automatically ensure the imaging subsystem is operating at a desired rate.

15. The system of claim 1 in which the controller is configured to automatically ensure illumination of at least capillary bed is within a predetermined illumination range.

16. The system of claim 1 in which the controller is configured to control one or more light sources of the imaging system to emit light at one or more selected wavelengths or wavelength ranges.

17. The system of claim 16 in which the controller is configured to select one or more wavelengths or wavelength ranges based on image quality.

18. The system of claim 1 in which the controller activates or not activates the imaging system based on the quality of the images of the capillary bed.

19. The system of claim 1 in which the controller activates the imaging system to acquire the images including one or more capillaries in the capillary bed for a period of time based on the number of optical adsorption gaps (OAGs) detected in one or more capillaries.

20. The system of claim 1 in which the controller communicably coupled to the imaging subsystem is configured to detect finger movement in the platform by the imaging subsystem.

21. A method for acquiring images of one or more capillaries in a capillary bed, the method comprising:
    receiving a body portion of a human subject;
    acquiring images of at least a capillary bed of the body portion with a repositionable field of view;
    automatically repositioning the field of view to different areas of the capillary bed;
    at each field of view within the capillary bed, acquiring images of one or more capillaries in the capillary bed;
    processing the images of each said area and assigning a location and confidence level of one or more high-quality capillaries in each said area; and
    wherein information from each field of view is stitched together to produce a distribution of capillary locations, capillary sizes, and confidence levels of capillary existence across a super field of view.

22. The method of claim 21 further including processing said distribution of capillary locations and confidence levels and determining a location and/or size of an optimum field of view for recording a set of images of high-quality capillaries.

23. The method of claim 21 in which images are stitched together by the controller across a super field of view to produce a single image and detecting capillary locations, sizes, and confidence levels in that single image.

24. The method of claim 21 in which the super field of view capillary distribution plot is acquired from a middle bottom location of a nailfold.

25. The method of claim 21 further including automatically calibrating the imaging to a predetermined start location.

26. The method of claim 21 further including automatically adjusting the exposure time.

27. The method of claim 21 further including automatically adjusting imaging system gain.

28. The method of claim 21 further including automatically adjusting the focus.

29. The method of claim 21 further including automatically ensuring the imaging is at a desired rate.

30. The method of claim 21 further including automatically ensuring the illumination of at least the capillary bed is within a predetermined illumination range.

31. The method of claim 21 including automatically ensuring the exposure time is within a predetermined exposure time range.

32. The method of claim 21 including automatically ensuring the imaging system gain is within a predetermined range.

33. The method of claim 21 including automatically ensuring focusing is within a predetermined focusing range then automatically emitting light at one or more selected wavelengths or wavelength ranges.

34. The method of claim 33 in which selecting the one or more wavelengths or wavelength ranges is based on image quality.

35. The method of claim 21 including activating or not activating the imaging based on the quality of images in the capillary bed.

36. The method of claim 21 including acquiring the images of one or more capillaries in the capillary bed for a period of time based on the number of optical absorption gaps detected in the one or more capillaries.

37. The method of claim 21 including detecting movement of a finger during the imaging.

* * * * *